(12) United States Patent
De Bruijn et al.

(10) Patent No.: US 11,471,073 B2
(45) Date of Patent: Oct. 18, 2022

(54) RESPIRATORY MOTION DETECTION APPARATUS

(75) Inventors: Frederik Jan De Bruijn, Eindhoven (NL); Adrienne Heinrich, Eindhoven (NL); Ruud Vlutters, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 659 days.

(21) Appl. No.: 13/641,906

(22) PCT Filed: Apr. 13, 2011

(86) PCT No.: PCT/IB2011/051595
§ 371 (c)(1),
(2), (4) Date: Oct. 18, 2012

(87) PCT Pub. No.: WO2011/132118
PCT Pub. Date: Oct. 27, 2011

(65) Prior Publication Data
US 2013/0035599 A1   Feb. 7, 2013

(30) Foreign Application Priority Data
Apr. 21, 2010   (EP) ...................................... 10160571

(51) Int. Cl.
*A61B 5/113*        (2006.01)
*G06T 7/521*        (2017.01)

(52) U.S. Cl.
CPC ............ *A61B 5/1135* (2013.01); *G06T 7/521* (2017.01); *G06T 2207/10016* (2013.01); *G06T 2207/30004* (2013.01)

(58) Field of Classification Search
CPC .............................. A61B 5/113; A61B 5/0064
See application file for complete search history.

(56) References Cited

U.S. PATENT DOCUMENTS 4,967,751 A * 11/1990 Sterzer ........................ 600/407
5,107,845 A    4/1992 Guern et al.
(Continued)

FOREIGN PATENT DOCUMENTS

DE    102004033907 A1    2/2006
EP       1410755 A1      4/2004
(Continued)

OTHER PUBLICATIONS

De Boer et al. "Structured Light Plethysmography" BMVC 2010 pp. 1-10.*
(Continued)

*Primary Examiner* — Allen Porter
*Assistant Examiner* — Michael A Catina

(57) ABSTRACT

The invention relates to a respiratory motion detection apparatus (1) for detecting respiratory motion of a person. An illuminator (3) illuminates the person (2) with an illumination pattern (11), and a detector (4) detects the illumination pattern (11) on the person (2) over time. A temporal respiratory motion signal being indicative of the respiratory motion of the person (2) is determined from the detected illumination pattern by a respiratory motion signal determination unit (5). The illumination pattern deforms significantly with slight movements of the person. Thus, since the respiratory motion signal determination unit (5) is adapted to determine the temporal respiratory motion signal from the detected illumination pattern, even slight respiratory movements of the person can be determined. The sensitivity of detecting respiratory movements of a person can therefore be improved.

17 Claims, 10 Drawing Sheets

(56) References Cited

U.S. PATENT DOCUMENTS

| | | | |
|---|---|---|---|
| 6,352,517 B1 | 3/2002 | Flock | |
| 6,492,634 B2* | 12/2002 | Marchitto | A61B 5/113 250/221 |
| 2005/0131607 A1* | 6/2005 | Breed | B60N 2/002 701/45 |
| 2006/0162074 A1* | 7/2006 | Bader | A47C 27/082 5/421 |
| 2006/0279428 A1 | 12/2006 | Sato et al. | |
| 2008/0077015 A1* | 3/2008 | Boric-Lubecke et al. | 600/453 |
| 2008/0243019 A1 | 10/2008 | Tsujimura | |
| 2009/0039235 A1 | 2/2009 | Macfarlane et al. | |
| 2009/0187112 A1* | 7/2009 | Meir et al. | 600/534 |
| 2010/0152600 A1* | 6/2010 | Droitcour | A61B 5/1114 600/534 |
| 2010/0210931 A1* | 8/2010 | Cuccia et al. | 600/328 |

FOREIGN PATENT DOCUMENTS

| | | |
|---|---|---|
| EP | 1645840 B1 | 11/2009 |
| JP | 2003032672 A | 1/2003 |
| JP | 2008253765 A | 10/2008 |
| JP | 2008264237 A | 11/2008 |

OTHER PUBLICATIONS

D.H. Brand, E. Lau et al. Measurement of Tidal Breathing: a Comparison of Structtured Light Plethysmography with Pneumatachography, Nov. 2009, Conference: Winter Meeting of the British-Thoracic-Society, vol. 64.*

De Haan, Gerard et al "True-Motion Estimation with 3-D Recursive Search Block Matching" IEEE Transactions on Circuits and Systems for Video Technology, vol. 3, No. 5, Oct. 1993. pp. 368-379.

Wyant, J.C. "Phase-Shifting Interferometry" University of Arizona, Course Material, 1998. pp. 1-16.

The Merck Manuals—Online Medical Library, Downloaded From http://www.merck.com on Mar. 4, 2016. 1 Page Document.

Dickstein et al, "ESC Guidelines for the Diagnosis and Treatment of Acute and Chronic Heart Failure 2008", European Journal of Heart Failure, 2008, pp. 933-989.

HFSA, "Heart Failure Facts", Downloaded From http://www.hfsa.org on Mar. 4, 2016, pp. 1-3.

U.S. Department of Health and Human Services; "Your Guide to Healthy Sleep", Downloaded From http://www.nhlbi.nih.gov/health/public/sleep/healthy_sleep.pdf on Mar. 3, 2016.

Ad Instruments, Software and Hardware Products for Life Science, Downloaded From http://www.adinstruments.com/products/product.php?id=mlt1132, Mar. 4, 2016, pp. 1-4.

Harada et al, "Sensor Pillow System: Monitoring Respiration and Body Movement in Sleep", Proceedings of 2000 IEEE/RSJ International Conference on Intelligent Robots and Systems, vol. 1, 2000, pp. 351-356.

Bhanu et al, "Kinematic-Based Human Motion Analysis in Infrared Sequences", Proceedings of the Sixth IEEE Workshop on Applications of Computer Vision, 2002, pp. 208.

Han et al, "Fusion of Colorand Infrared Video for Moving Human Detection", Pattern Recognition, vol. 40, 2007, pp. 1771-1784.

Liao et al, "Homomorphic Processing Techniques for Near-Infrared Images", ICASSP, 2003, pp. III-461-III-464.

Wang, "Real Time Sobel Square Edge Detector for Night Vision Analysis", ICIAR, LNCS 4141, 2006, pp. 404-413.

Kuo et al, "Artifical Neural Networks Based Sleep Motion Recognition Using Night Vision Cameras", Biomedical Engineering—Application, Basis & Communications, vol. 16, No. 2, 2004, pp. 37-44.

Bradski et al, "Motion Segmentation and Pose Recognition with Motion History Gradients", Machine Vision and Applications, vol. 13, 2002, pp. 174-184.

Han et al, "Human Activity Recognition in Thermal Infrared Imagery", Proceedings of Computer Vision and Pattern Recognition, 2006, pp. 1-8.

Liao et al, "Video-Based Activity and Movement Pattern Analysis in Overnight Sleep Studies", ICPR, 2008, pp. 1-4.

Wang et al, Artificial Intelligent Vision Analysis in Obstructive Sleep Apnoea (OSA), University of Lincoln, Poster, Undated, 1 Page.

Nakajima et al, "A Monitor for Posture Changes and Respiration in Bed Using Real Time Image Sequence Analysis", Engineering in Medicine and Biology Society, vol. 1, 2000, pp. 51-54.

* cited by examiner

RESPIRATORY MOTION DETECTION APPARATUS

FIELD OF THE INVENTION

The invention relates to a respiratory motion detection apparatus, respiratory motion detection method and respiratory motion detection computer program for detecting respiratory motion of a person.

BACKGROUND OF THE INVENTION

DE 10 2004 033 907 A1 discloses an apparatus for monitoring a patient in a home environment as regards to breathing interruptions and/or snoring. The apparatus comprises an infrared light source for illuminating the patient and an infrared camera for capturing infrared images from the patient. The apparatus further comprises a directional microphone for detecting breathing sounds of the patient. The captured infrared images and detected breathing sounds are used for determining breathing interruptions and/or snoring.

The additional directional microphone is needed for detecting breathing sounds, because the sensitivity of the infrared detection system is too low for determining breathing interruptions and/or snoring.

SUMMARY OF THE INVENTION

It is an object of the present invention to provide a respiratory motion detection apparatus, respiratory motion detection method and respiratory motion detection computer program for detecting respiratory motion of a person, wherein the sensitivity of detecting respiratory motion by using a light detector can be improved.

In a first aspect of the present invention a respiratory motion detection apparatus for detecting respiratory motion of a person is presented, wherein the respiratory motion detection apparatus comprises:
  an illuminator for illuminating the person with an illumination pattern,
  a detector for detecting the illumination pattern on the person over time,
  a respiratory motion signal determination unit for determining a temporal respiratory motion signal being indicative of the respiratory motion of the person from the detected illumination pattern.

The illumination pattern deforms significantly with slight movements of the person, which are hardly detectable in, for example, temporally consecutive images of a person who is not illuminated with an illumination pattern. Since the respiratory motion signal determination unit is adapted to determine the temporal respiratory motion signal from the detected illumination pattern, i.e. from the deformation of the illumination pattern, even slight respiratory movements of the person can be determined. The sensitivity of detecting respiratory movements of a person can therefore be improved.

The respiratory detection apparatus determines the respiratory motion of the person preferentially unobtrusively. Sensors attached to the person are preferentially not required. The respiratory motion detection apparatus can be installed at a remote distance. Generally, no specific location is obliged as long as the person is in line-of-sight, as is the case, for example, with a sensor in a pillow or under a mattress of a bed. For detecting respiratory motion the illumination pattern is preferentially projected at least on the chest of the person. Since the illumination pattern is very sensitive to motion of the chest of the person, the respiratory motion detection apparatus can be adapted to detect both deep and shallow breathing of a person.

The illuminator is preferentially adapted to project the illumination pattern onto the person which may lie in a bed. The detector is preferentially a video camera for capturing images of the person showing the illumination pattern over time. The detector captures therefore preferentially a video of the illumination pattern showing deformations of the illumination pattern caused by respiratory movements of the person.

The illuminator can be adapted to illuminate one or several persons with the illumination pattern, wherein the detector can be adapted for capturing the illumination pattern on the one or more persons over time. The respiratory motion signal determination unit is then preferentially adapted to determine several temporal respiratory motion signals being indicative of the respiratory motion of the respective person from the detected illumination pattern covering several persons. The respiratory motion signal associated with a person is preferentially a data stream, i.e., if several persons are illuminated by the illumination pattern, for different persons different data streams are determined being indicative of the respiratory motion of the respective person.

Preferentially, it is not necessary that the illumination pattern is projected directly onto the person, i.e. onto the skin of the person. The illuminator can be adapted to project the illumination pattern on a surface which moves with the respiratory motion of the person. The surface is, for example, the surface of clothes of the person or of a blanket covering the person. The illuminator is therefore preferentially adapted to project the illumination pattern on a bed in which a person is lying.

The illuminator is preferentially adapted to illuminate the person with a stationary illumination pattern. The illuminator can be based on a slide projector for generating the illumination pattern, i.e. the textured light pattern. The illuminator can include a projection system for projecting light in a perimeter of 360 degrees, wherein the detector can be a camera that captures the illuminated area. Such a camera can be built using wide angle optics optionally based on a convex reflector lens. The illuminator can also comprise a coherent light source such as a laser and diffractive optics to create a sharp illumination pattern on the person. Such an illumination pattern is generally not subject to defocus blur or lens aberrations.

The illuminator is preferentially adapted to illuminate the person with an illumination pattern being invisible for human beings. The illuminator is preferentially adapted to illuminate the person with infrared light, in particular, with near infrared light, and the detector is preferentially an infrared camera, in particular, a near-infrared camera, for capturing images of the person over time showing the illumination pattern. The illuminator is, for example, a light emitting diode emitting near infrared light. A person is therefore not disturbed by the illumination with the illumination pattern. For example, if the person is a sleeping person, the sleep of the person is not disturbed by the illumination pattern.

In a further embodiment, the illuminator can be adapted to generate ultraviolet light for illuminating the person with an ultraviolet illumination pattern. In this case, the detector is adapted to detect the ultraviolet illumination pattern on the person. In particular, the detector is an ultraviolet video camera for capturing a video of the ultraviolet illumination pattern.

In an embodiment, the illuminator comprises an illumination source and a spatial light modulator. The illumination source can be an incoherent light source like a light emitting diode, which preferentially emits infrared light. If the illumination source is an incoherent light source, the spatial light modulator is preferably an attenuating mask or slide. If the illumination source is a coherent light source like a laser, which emits preferentially infrared light, the spatial light modulator is preferentially an attenuating mask and/or a diffractive element. The last implementation has the advantage that always a sharp projected illumination pattern can be obtained, regardless the distance between illuminator and illuminated surface. Also in this embodiment, the illumination source can be adapted to emit ultraviolet light instead of the preferred infrared light.

The respiratory motion detection apparatus can comprise an output unit for outputting an output signal depending on the determined respiratory motion signal. The output signal can be adapted to influence the person depending on the determined respiratory motion signal. For example, a person's sleep/relaxation state can be influenced by a change in sound, light, temperature and/or air composition provided by the output signal. Moreover, if the determined respiratory motion signal is indicative of irregularities in respiration, the person can be alerted by the output signal and, for example, a doctor's visit can be suggested.

It is preferred that the illuminator is adapted to illuminate the person in an illumination direction and the detector is adapted to detect the illumination pattern on the person in a detection direction, wherein the illumination direction and the detection direction are different. The illuminator and the detector are therefore preferentially arranged at different locations. For example, the illuminator and the detector can have a distance of about 10 cm.

It is further preferred that the illuminator and the detector are adapted to allow a) the illuminator to illuminate a surface of the person with the illumination pattern under an illumination angle being defined as the angle between the illumination direction and an axis being perpendicular to the illuminated surface, and b) the detector to detect the illumination pattern on the surface under a detection angle being defined as the angle between the detection direction and an axis being perpendicular to the illuminated surface, wherein the illumination angle is larger than the detection angle. In an embodiment, the illumination angle is 90 degrees and the detection angle is larger than 0 degrees and smaller than 90 degrees. This further improves the sensitivity of the detected illumination pattern to respiratory movements of the person and, thus, the sensitivity of the respiratory motion detection apparatus.

In a preferred embodiment, the illuminator and the detector are adapted to allow the illuminator to illuminate a surface of the person with the illumination pattern under an illumination angle being larger than 70 degrees, and the detector to detect the illumination pattern on the surface under a detection angle being smaller than 20 degrees. It is further preferred that the illumination angle is larger than 80 degrees and it is even further preferred that the illumination angle is larger than 85 degrees. Moreover, it is further preferred that the detection angle is smaller than 10 degrees and it is even further preferred that the detection angle is smaller than 5 degrees. This further increases the sensitivity of detecting respiratory motion.

The illuminator and the detector are preferentially pre-aligned such that the apparent motion of the detected illumination pattern is larger in magnitude than the apparent motion of the person, in particular, of the respiratory motion of the person. Preferentially, for different positions and orientations of the illuminator and/or different positions and orientations of the detector the apparent motion of the detected illumination pattern and the apparent motion of the person are detected and the position and orientation of the illuminator and/or the position and the orientation of the detector are chosen, for which the difference in magnitude between the apparent motion of the detected illumination pattern and the apparent motion of the person is optimized.

It is preferred that the detector is adapted to detect several images of the illumination pattern at different times, wherein the respiratory motion signal determination unit is adapted to determine the temporal respiratory motion signal depending on the sum of the absolute differences of image values of corresponding positions in temporally consecutive images. This means that image values, which correspond to the same position within temporally consecutive images, are subtracted from each other for generating several differences for two temporally consecutive images of the illumination pattern, and that the absolute values of these differences are summed up for generating a respiratory motion signal at the time at which the two temporally consecutive images have been captured. This time is, for example, the average of the times at which the two temporally consecutive temporally consecutive images have been acquired, or the time at which the first or the second of the two temporally consecutive images has been captured. By determining the respiratory motion signal for several pairs of temporally consecutive image of the illumination pattern, the temporal respiratory motion signal can be calculated. This allows the respiratory motion detection apparatus to calculate the respiratory motion signal in a simple way with only low computational costs.

In a further embodiment, the respiratory motion signal determination unit is adapted to determine the temporal respiratory motion signal depending on the sum of the absolute differences of image values of corresponding positions in temporally close images, which do not have to be temporally consecutive images. In an embodiment, one image can be used as a reference image, wherein the location of the reference image in the respiration cycle has been identified. For example, the image at the moment of an expiratory pause can serve as a reference image for following images of the same and/or other respiration cycles. Also the image at an inhale/exhale transition can be used as a reference image. Then, the sum of absolute differences (SAD) between the reference image and the following images can be computed for determining the respiratory motion signal which can also be regarded as a breathing waveform or from which a breathing waveform can be derived.

The respiratory motion detection apparatus is preferentially adapted to low-pass filter the respiratory motion signal. This allows the respiratory motion detection apparatus to smooth the respiratory motion signal and to reduce noise. The respiratory motion signal is preferentially low-pass filtered for determining exhale/inhale transitions as will be described further below.

It is further preferred that the respiratory motion detection apparatus comprises a respiratory characteristics determination unit for determining a respiratory characteristic of the person from the determined temporal respiratory motion signal. This allows the respiratory motion detection apparatus to determine respiratory characteristics with high accuracy and unobtrusively.

The respiratory characteristics determination unit can be adapted to determine at least one of the respiration cycle, the period of inhaling, the period of exhaling, the inhale-exhale transitions and the exhale-inhale transitions.

The respiratory characteristics determination unit can be adapted to determine a sleep efficiency index, if the respiratory motion signal is generated while the person is sleeping. The sleep efficiency index can be provided to the person, after the person has woken up. The sleep efficiency index can be determined from a person's sleeping pattern determined from the respiratory motion signal. The sleep efficiency index can be computed as the ratio of the total sleep time and the time in bed. The time in bed can be determined by using the pattern deformation as an indicator. When the pattern is not deformed, no person is present. The total sleep time can be estimated from a respiration and actigraphy analysis performed by processing captured images of the illumination pattern. The total sleep time can be computed in the same manner as is done with accelerometers or ActiWatches made by Philips Respironics and usually worn around a person's wrist. Such a method is disclosed, for example, in "The Harvard Medical School Guide to a Good Night's Sleep" by Lawrence J. Epstein et al., The McGraw Hill Companies (2007).

It is preferred that the respiratory characteristics determination unit is adapted to determine inhale/exhale transitions and exhale/inhale transitions depending on the times at which the respiratory motion signal shows a local minimum. Since the local minimum can easily be detected, the respiratory motion detection apparatus can determine the inhale/exhale and exhale/inhale transitions with low computational costs.

It is further preferred that the respiratory characteristics determination unit is adapted to determine the inhale/exhale transitions depending on high-frequent local minima and to determine the exhale/inhale transitions depending on low-frequent local minima. High-frequent local minima correspond to a larger temporal frequency and have a smaller distance to neighboring local maxima in comparison to low-frequent local minima, which correspond to a smaller temporal frequency and have a larger distance to neighboring local maxima. For example, a distance threshold or frequency threshold can be defined and, if the longest distance of a local minimum to two neighboring local maxima is smaller than the distance threshold or the frequency to which the local minimum corresponds is larger than the frequency threshold, the local minimum is preferentially used for determining an inhale/exhale transition, and if this longest distance is larger than the distance threshold or this frequency is smaller than the frequency threshold, the local minimum is preferentially used for determining an exhale/inhale transition. The distance threshold and/or the frequency threshold can be determined by calibrating the respiratory motion detection apparatus with a respiratory motion signal and known temporal positions and/or frequency positions of the inhale/exhale and exhale/inhale transitions.

In a further embodiment, the respiratory characteristics determination unit is adapted to determine the inhale/exhale transitions by determining a time of an exhale/inhale transition and by using an image of the illumination pattern captured at this time as a reference frame, wherein the largest sum of absolute differences between the reference frame and the following frames, i.e. of following video images of the illumination pattern, within one breathing cycle corresponds to the inhale/exhale transition following the determined exhale/inhale transition. The sum of absolute differences between the reference frame and a following frame can be defined by following equation:

$$SAD(n, n+i) = \sum_{(x,y) \in W} |I_n(x, y) - I_{n+i}(x, y)|, \qquad (1)$$

wherein n denotes the number of the reference image, i.e. the frame number of the reference image which can also be regarded as a reference frame, i the number of images between the reference image and one of the following images which can also be regarded as a frame, x, y denote pixel coordinates in the images $I_n$ and $I_{n+i}$, respectively, and W denotes all possible pixel coordinates.

It is preferred that the respiratory characteristics determination unit is adapted to
  low-pass filter the respiratory motion signal such that the high-frequent minima are filtered out,
  determine the local minima of the low-pass filtered respiratory motion signal,
  determine the exhale/inhale transitions from the determined local minima. Also this allows the respiratory motion detection apparatus to determine the exhale/inhale transitions with low computational costs. The low-pass filter can be determined by calibrating the respiratory motion detection apparatus with a respiratory motion signal comprising known frequencies corresponding to the inhale/exhale and the exhale/inhale transitions. The low-pass filtering can be performed by convolving the respiratory motion signal with a box or rectangle filter or another filter for eliminating the high-frequent minima. The determination of the local minima can be performed by convolving the low-pass filtered respiratory motion signal with the first order Gaussian derivative or similar filters and by determining the zero crossings of the resulting signal. A +/− zero crossing defines a local maximum and a −/+ zero crossing defines a low-frequent local minimum.

It is further preferred that the respiratory characteristics determination unit is adapted to
  calculate a streaming standard deviation of the respiratory motion signal,
  determine local maxima of the calculated streaming standard deviation,
  determine peak positions of peaks of the calculated streaming standard deviation having an amplitude larger than a predefined threshold,
  determine for each local maximum of the local maxima a peak position among the determined peak positions, which is closest to the position of the respective local maximum, and
  determine the inhale/exhale transitions from the determined peak positions. The predefined threshold is preferentially determined experimentally, in particular, by calibration measurements.

It is further preferred that the respiratory characteristics determination unit is adapted to weight the calculated streaming standard deviation before determining the positions of peaks, wherein the weight for a calculated streaming standard deviation value is larger, if the corresponding respiratory motion signal value is located in a local minimum or valley of the respiratory motion signal, and wherein the weight for a calculated streaming standard deviation value is smaller, if the corresponding respiratory motion signal value is not located in a local minimum or valley of the respiratory motion signal. The larger weight is, for example, 1000 and the smaller weight is, for example, one. For determining, whether a certain respiratory motion signal value is located in a local minimum or a valley of the respiratory motion signal, the respiratory characteristics determination unit can be adapted to determine whether a) the sum of respiratory motion signal values in a first region close, in particular, around the certain respiratory motion signal value, is smaller than the sum of respiratory motion signal values in a second region being neighbored to the first region in a temporal backward direction and b) the sum of respiratory motion signal values in a third region close, in particular, around the certain respiratory motion signal value, is smaller than the sum of respiratory motion signal values in a fourth region being neighbored to the third region in a temporal forward direction. For example, if the certain respiratory motion signal value corresponds to the frame number n, the first region can be defined by the frame numbers n−1 and n, the second region can be defined by the frame numbers n−3 and n−2, the third region can be defined by the frame numbers n+1 and n, and the fourth region can be defined by the frame numbers n+3 and n+2. The first region and the third region can be the same.

It is further preferred that the illuminator is adapted to illuminate the person with at least one of a sinusoidal illumination pattern and a saw-tooth illumination pattern. A sinusoidal pattern and saw-tooth illumination pattern are very sensitive to movements of the persons, i.e. even very small movements of the person lead to significant deformations of the illumination pattern. By using a sinusoidal illumination pattern and/or a saw-tooth illumination pattern the sensitivity of the respiratory motion detection apparatus can therefore further be improved.

It is further preferred that the illuminator is adapted to illuminate the person with an illumination pattern being a repetitive pattern in one or more spatial directions. It is preferred that the illuminator is adapted to illuminate the person with a spatially high-frequent illumination pattern. The more high-frequent the illumination pattern, the more sensitive the breathing analysis can be performed, in particular, due to larger differences in the computation of the sum of absolute differences between two frames. In an embodiment, the spatial frequency of the illumination pattern is chosen as high as possible, but at a value that is not attenuated due to the modulation transfer function of the optical system of the detector, in particular, of the camera.

The respiratory motion detection apparatus can comprise a respiratory motion filtering unit for filtering the temporal respiratory motion signal such that influences on the temporal respiratory motion signal due to other motions of the person are reduced, in particular, eliminated. This respiratory motion signal filtering unit can be calibrated by performing calibration measurements with known respiratory movements and known non-respiratory movements of the person.

It is further preferred that the respiratory motion detection apparatus is adapted to detect the respiratory motion of several persons, wherein the illuminator is adapted to illuminate the several persons by the illumination pattern, and
the respiratory motion signal determination unit is adapted to assign different regions of the detected illumination pattern to the several persons and to determine the respiratory motion signal of a person of the several persons from the region of the detected illumination pattern assigned to the respective person. Thus, different spatial regions of the detected illumination pattern, i.e. of a video showing the deformations of the illumination pattern, are identified and assigned to the several persons, and the respiratory motion signals of the persons are determined based on the deformations of the illumination pattern in the different spatial regions of the detected illumination pattern. This allows the respiratory motion detection apparatus to determine the respiratory motions of different persons in a room, in particular, lying in one or multiple beds.

In a further aspect of the present invention a respiratory motion detection method for detecting respiratory motion of a person is presented, wherein the respiratory motion detection method comprises:

illuminating the person with an illumination pattern,
detecting the illumination pattern on the person over time,
determining a respiratory motion signal being indicative of the respiratory motion of the person from the detected illumination pattern.

In a further aspect of the present invention a respiratory motion detection computer program for detecting respiratory motion of a person is presented, wherein the computer program comprises program code means for causing a respiratory motion detection apparatus as defined in claim 1 to carry out the steps of the respiratory motion detection method as defined in claim 14, when the computer program is run on a computer controlling the respiratory motion detection apparatus.

It shall be understood that the respiratory motion detection apparatus of claim 1, the respiratory motion detection method of claim 14 and the respiratory motion detection computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
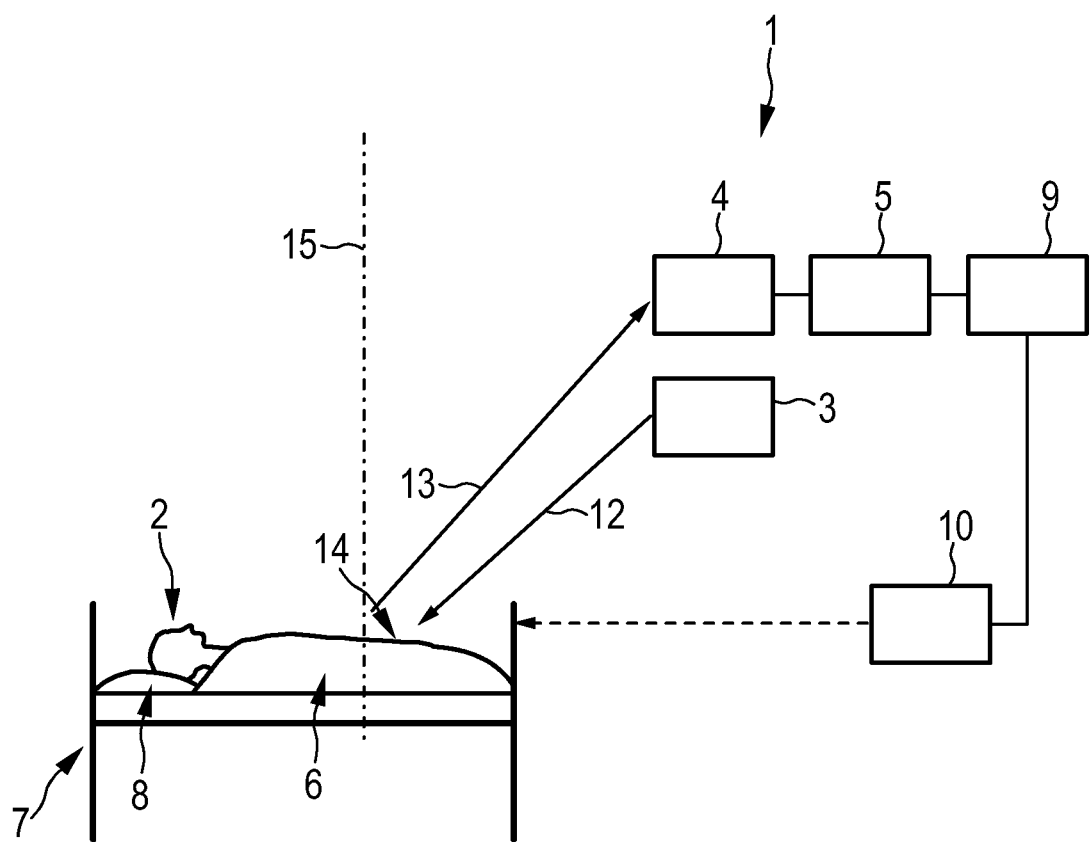
FIG. 1 shows schematically and exemplarily an embodiment of a respiratory motion detection apparatus for detecting respiratory motion of a person.

FIG. 1 shows schematically and exemplarily an embodiment of a respiratory motion detection apparatus 1 for detecting respiratory motion of a person 2. The person 2 is lies in a bed 7, wherein the head of the person 2 is located on a pillow 8 and the person 2 is covered by a blanket 6. The respiratory motion detection apparatus 1 comprises an illuminator 3 for illuminating the person 2 with an illumination pattern, a detector 4 for detecting the illumination pattern on the person 2 over time, and a respiratory motion signal determination unit 5 for determining a temporal respiratory motion signal being indicative of the respiratory motion of the person 2 from the detected illumination pattern. The respiratory motion detection apparatus is installed at a remote distance, for example, at a ceiling, a wall or a floor of a room in which the bed 7 is located.

The illuminator 3 is adapted to illuminate the chest of the person 2 with the illumination pattern. In particular, the part of the blanket 6 is illuminated by the illumination pattern, which covers the chest of the person 2. Since deformations of the detected illumination pattern are very sensitive to motion of the chest of the person 2, the respiratory motion detection apparatus 1 can be adapted to detect both deep and shallow breathing of the person 2.

The illuminator 3 is adapted to illuminate the person 2 with a stationary illumination pattern. The illuminator 3 can comprise a slide projector for generating the illumination pattern, i.e. the textured light pattern. The illuminator 3 can include a projection system for projecting light in a perimeter of 360 degrees, wherein the detector 4 can be a video camera that captures the illuminated area. Such a video camera can be built by using wide angle optics optionally based on a convex reflector lens. The illuminator 3 can also comprise a coherent light source like a laser or a light emitting diode and diffractive optics to create a sharp illumination pattern on the person 2.

Figure 2:
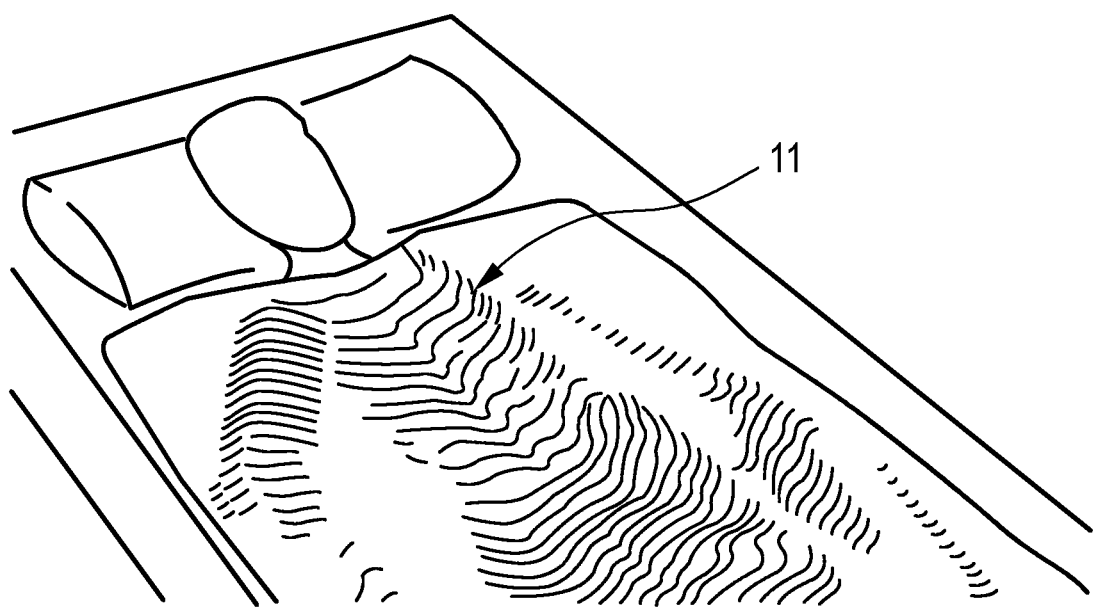
FIG. 2 shows schematically and exemplarily an illumination pattern.

The illuminator 3 is adapted to illuminate the person 2 with infrared light, in particular, with near infrared light, or with ultraviolet light. The illuminator 3 can be adapted to illuminate the person with a repetitive pattern in one or more spatial directions. In particular, the illuminator 3 can be adapted to illuminate the person 2 with at least one of a sinusoidal illumination pattern and a saw-tooth illumination pattern. The illumination pattern is preferentially spatially high-frequent. An exemplary illumination pattern 11 on the person is shown in FIG. 2.

The detector 4 is a video camera for capturing video images of the illumination pattern 11 on the person 2, in particular, on the blanket 6 of the person 2, over time. The detector 4 captures therefore a video of the illumination pattern 11 showing deformations of the illumination pattern 11 caused by respiratory movements of the person 2. In this embodiment, the illuminator 3 is preferentially adapted to illuminate the blanket 6, which covers the person 2, with an infrared illumination pattern, wherein the detector 4 is an infrared sensitive video camera for detecting the infrared illumination pattern on the blanket 6, in particular, for detecting deformations of the infrared illumination pattern on the blanket 6 generated by respiratory motion of the person 2.

The illuminator 3 is adapted to illuminate the person 2, in particular, the blanket 6 covering the person 2, in an illumination direction 12 and the detector 4 is adapted to detect the illumination pattern on the person 2 in a detection direction 13, wherein the illumination direction 12 and the detection direction 13 are different. Preferentially, the illuminator 3 and the detector 4 are adapted to allow the illuminator 3 to illuminate a surface 14 of the person 2 with the illumination pattern under an illumination angle being larger than 70 degrees, wherein the illumination angle is defined as the angle between the illumination direction 12 and an axis 15 being perpendicular to the illuminated surface 14, and to allow the detector 4 to detect the illumination pattern on the surface 14 under a detection angle being smaller than 20 degrees, wherein the detection angle is defined as the angle between the detection direction 14 and an axis 15 being perpendicular to the illuminated surface 14. It is further preferred that the illumination angle is larger than 80 degrees and it is even further preferred that the illumination angle is larger than 85 degrees. Moreover, it is also preferred that the detection angle is smaller than 10 degrees and it is even further preferred that the detection angle is smaller than 5 degrees. It is therefore preferred that the illumination angle is almost 90 degrees and that the detection angle is almost 0 degrees. This configuration causes the observed illumination pattern to move with a larger amplitude than the observed motion of the surface itself. This will in the following be illustrated with reference to FIGS. 3 and 4.

Figure 3:
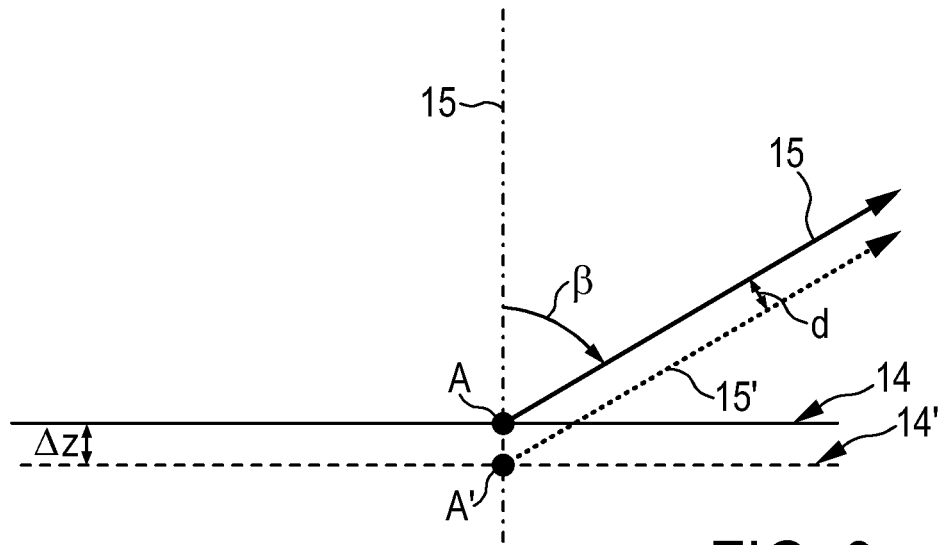
FIGS. 3 and 4 illustrate a magnification of a respiratory motion signal.

In FIG. 3, the surface 14 is not illuminated by a projected illumination pattern. If the surface 14 is moved to a location indicated in FIG. 3 by 14' over a distance Δz, the detector detects this movement under a detection angle β as a movement of the ray 15 over the distance d to the location indicated in FIG. 3 by 15'. In FIG. 3, the ray 15 originates from the point A and the shifted ray at the location indicated by 15' originates from the position A' to which the point A has been moved.

Figure 4:
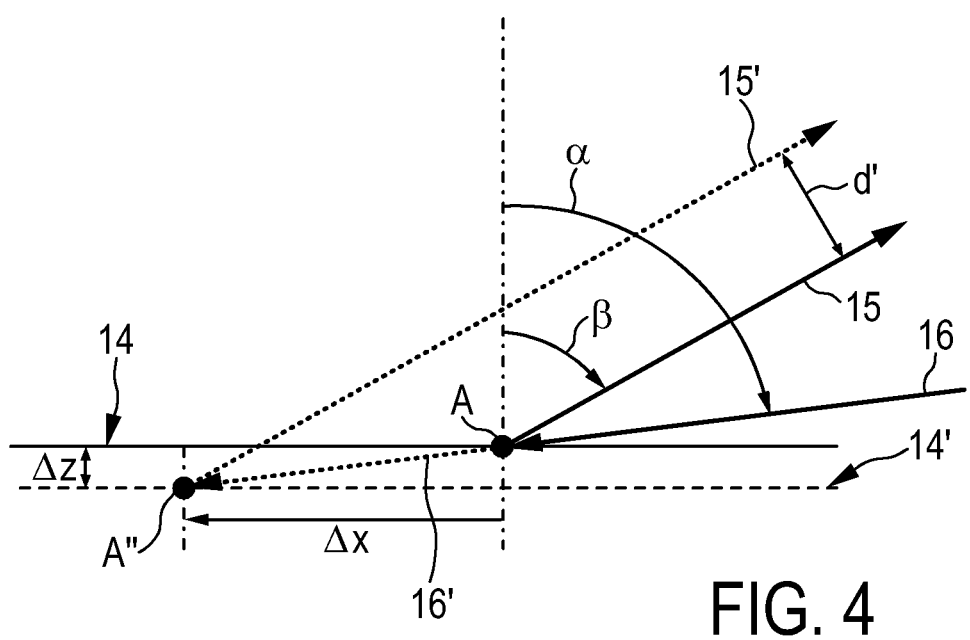

In FIG. 4, incident light 16 is projected under an illumination angle α and detected under a detection angle β on the surface 14. The surface 14 is shifted by the distance Δz to the position 14' such that the projected point A is shifted over a horizontal distance Δx to the point A". This shift is observed as an apparent shift d' projected in the detection direction of the detector by detecting the shift of the reflected ray 15 to the position indicated in FIG. 4 by 15'. In FIG. 4, reference number 16' indicates the incident light generating the illumination at the location A", after the surface 14 has been moved to the position indicated by reference number 14'. Since the distance d' is much larger than d, smaller vertical motions can be detected in the configuration shown in FIG. 4 in comparison to the configuration shown in FIG. 3.

In absence of a projected illumination pattern and corresponding to FIG. 3, the relation between the observed shift d and the real vertical shift Δz from A to A' can be described by following equation:

$$d = \Delta z \sin \beta \qquad (2)$$

The observed shift d defined by equation (2) can be regarded as an observed vertical shift, because this observed shift is caused by the real vertical shift Δz.

According to the configuration shown in FIG. 4, an illumination pattern is projected onto the surface 14 under the illumination angle α and the relation between the observed shift d' and the real vertical shift Δz from A to A" can be described by following equation:

$$d' = \Delta z \tan \alpha \cos \beta \qquad (3)$$

The advantage of the angulated projection can be expressed in terms of an increase of distance of the shifting phenomena as they appear on the detector, in particular, as they appear on the camera sensor. The resulting gain G can be defined as the ratio of the new displacement with respect to the old displacement in accordance with following equation:

$$G = \frac{d'}{d} = \frac{\Delta z \tan\alpha \cos\beta}{\Delta z \sin\beta} = \frac{\tan\alpha}{\tan\beta} \quad (4)$$

As can clearly be seen in equation (4), the gain G is maximized, if the illumination angle α, which could also be regarded as a projection angle, is as large as possible, in particular, almost parallel to the surface 14, and the detection angle β, which could also be regarded as an observation angle, is as small as possible, preferably with the detector's optical axis perpendicular to the surface 14.

It should be noted that the surface 14, on which the illumination pattern is projected, is of course generally not plane. The axis being perpendicular to the illuminated surface 14 is therefore preferentially an average of the normals to the illuminated surface.

The respiratory motion signal determination unit 5 is preferentially adapted to quantify the apparent motion of the illumination pattern and, thus, the respiratory motion of the person by calculating the SAD between consecutive video frames captured by the detector 4. The sequence of SAD values as a function of time is regarded as the temporal respiratory motion signal and preferentially virtually linearly proportional to the absolute value of the average velocity of the apparent motion of the illumination pattern. In particular, the detector 4 is adapted to detect several images of the illumination pattern at different times, wherein the respiratory motion signal determination unit 5 is adapted to determine the temporal respiratory motion signal depending on the sum of absolute differences of image values of corresponding positions in temporally consecutive images. This means that image values, which correspond to the same position within temporally consecutive images, are subtracted from each other for generating several differences for two temporally consecutive images of the illumination pattern, and that the absolute values of these differences are summed up for generating a respiratory motion signal at the time at which the two temporally consecutive images have been captured. This time is, for example, the average of the times at which the two temporally consecutive images have been acquired, or the time at which the first or the second of the two temporally consecutive images has been captured. By determining the respiratory motion signal for several pairs of temporally consecutive images of the illumination pattern, the temporal respiratory motion signal can be calculated in accordance with following equation:

$$\Delta_{lum}(n) = \sum_{x,y} |(f(x, y, n) - f(x, y, n-1))|, \quad (5)$$

wherein $\Delta_{lum}(n)$ denotes the absolute frame difference, i.e. the SAD, at the frame number n which is related to the time at which the respective frame has been captured. Pixel coordinates within a frame are indicated by x, y and the image value at the respective pixel coordinate, which can also be regarded as a luminance value, is denoted by f.

The respiratory motion detection apparatus 5 is preferentially adapted to low-pass filter the respiratory motion signal, in order to smooth the respiratory motion signal and to reduce noise.

Figure 5:
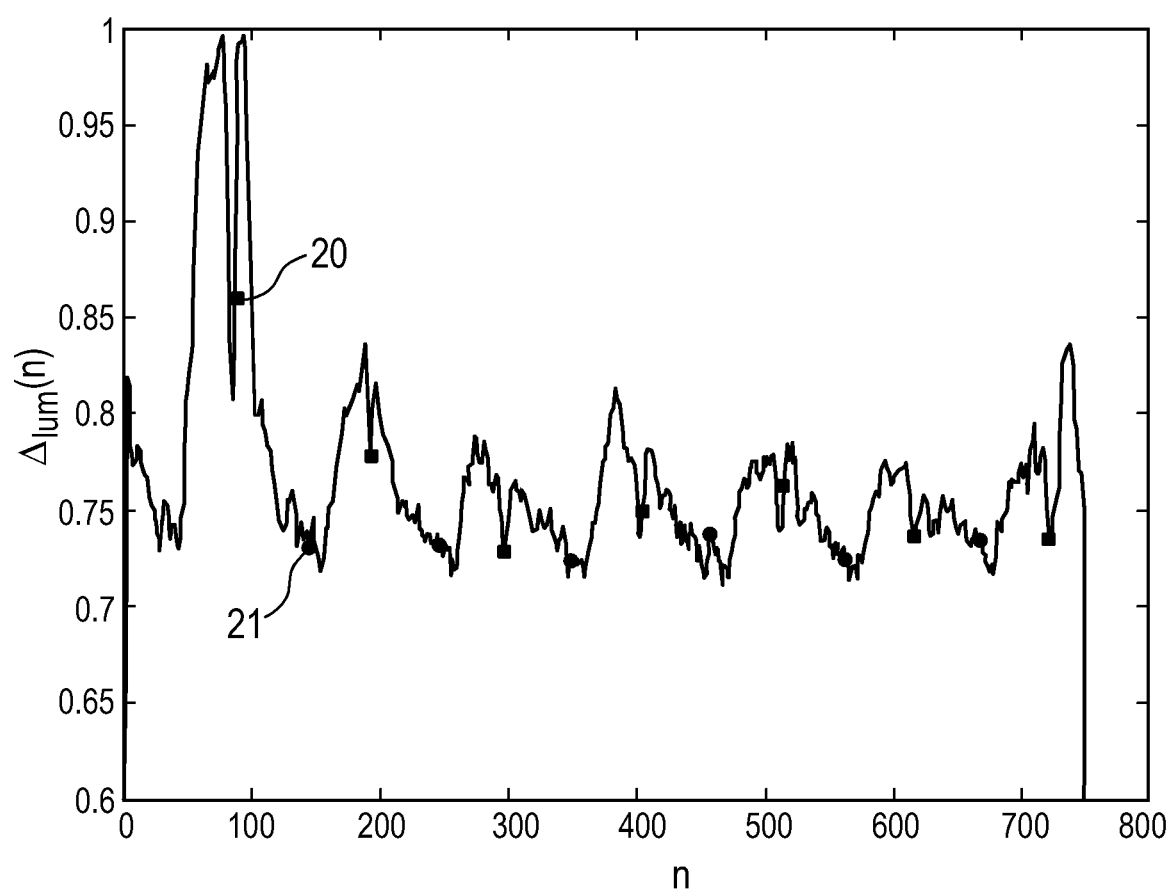
FIG. 5 shows schematically and exemplarily a slightly low-pass filtered respiratory motion signal.

FIG. 5 shows schematically and exemplarily a slightly low-pass filtered absolute frame difference $\Delta_{lum}(n)$ in normalized units. A stronger low-pass filter can be used to determine exhale/inhale transitions as will be described further below.

Referring again to FIG. 1, the respiratory motion detection apparatus 1 further comprises a respiratory characteristics determination unit 9 for determining a respiratory characteristic of the person 2 from the determined temporal respiratory motion signal being preferentially the absolute frame difference in accordance with equation (5). The respiratory characteristics determination unit 9 is preferentially adapted to determine at least one of the respiration cycle, the period of inhaling, the period of exhaling, the inhale/exhale transitions and the exhale/inhale transitions. Moreover, the respiratory characteristics determination unit 9 can be adapted to determine a sleep efficiency index, if the respiratory motion signal is generated, while the person is sleeping. The sleep efficiency index can be provided to the person, after the person has woken up. The sleep efficiency index can be computed as the ratio of the total sleep time and the time in bed. The time in bed can be determined by using the temporal respiratory motion signal as an indicator. If there is no temporal respiratory motion signal, it can be concluded that the person is not in the bed, i.e. the time in bed can be determined as the time period during which a temporal respiratory motion signal can be determined. For determining the total sleep time based on the temporal respiratory motion signal methods can be used which determine the total sleep time from accelerometer signals or ActiWatches made by Philips Respironics and usually worn around a person's wrist. Due to the unobtrusive nature of the proposed respiratory motion detection apparatus and method, and its inconspicuous and computationally low complex operation, the respiratory motion detection apparatus and method may open the gate to a variety of healthcare and consumer products.

The respiratory characteristics determination unit 9 is preferentially adapted to determine inhale/exhale transitions and exhale/inhale transitions depending on the times at which the respiratory motion signal shows a local minimum. The respiratory characteristics determination unit 9 is preferentially further adapted to determine at least one of a respiratory cycle, an inhale period and an exhale period from the determined inhale/exhale and exhale/inhale transitions. In particular, the respiratory characteristics determination unit 9 can be adapted to determine the inhale/exhale transitions depending on high-frequent local minima and to determine the exhale/inhale transitions depending on low-frequent local minima. High-frequent local minima correspond to a larger temporal frequency and have a smaller distance to neighboring local maxima in comparison to low-frequent local minima, which correspond to a smaller temporal frequency and have a larger distance to neighboring local maxima. For example, a distance threshold or frequency threshold can be defined and, if the longest distance of a local minimum to neighboring local maxima is smaller than the distance threshold or the frequency to which the local minimum corresponds is larger than the frequency threshold, the local minimum is preferentially used for determining an inhale/exhale transition, and if this longest distance is larger than the distance threshold or this frequency is smaller than the frequency threshold, the local minimum is preferentially used for determining an exhale/inhale transition. The distance threshold and/or the frequency threshold can be determined by calibrating the respiratory motion detection apparatus 1 with a respiratory motion signal and known temporal positions and/or frequency positions of the inhale/exhale and exhale/inhale transitions.

The inhale/exhale transitions are present at the locations where the respiratory motion signal as, for example, shown in FIG. 5 shows local minima, because there the illumination pattern hardly deforms in contrast to when a person's chest is moving due to inhaling or exhaling movements.

In FIG. 5 the inhale/exhale transitions are indicated by squares 20 and the exhale/inhale transitions are indicated by circles 21.

The respiratory characteristics determination unit 9 can be adapted to low-pass filter the respiratory motion signal such that the high-frequent minima are filtered out, wherein the local minima of the low-pass filtered respiratory motion signal are determined and the exhale/inhale transitions are determined from the determined local minima. The low-pass filter for filtering out high-frequent minima can be determined by calibrating the respiratory motion detection apparatus 1 with a respiratory motion signal comprising known frequencies corresponding to the inhale/exhale and exhale/inhale transitions. The low-pass filtering can be performed by convolving the respiratory motion signal $\Delta_{lum}(n)$ with a box or rectangle filter as described by following equation for eliminating the high-frequent minima:

$$\Delta_{lp\_lum}(n) = \Delta_{lum}(n) * \text{rect}(k) \tag{6}$$

wherein rect(k) denotes the box or rectangle filter.

Figure 6:
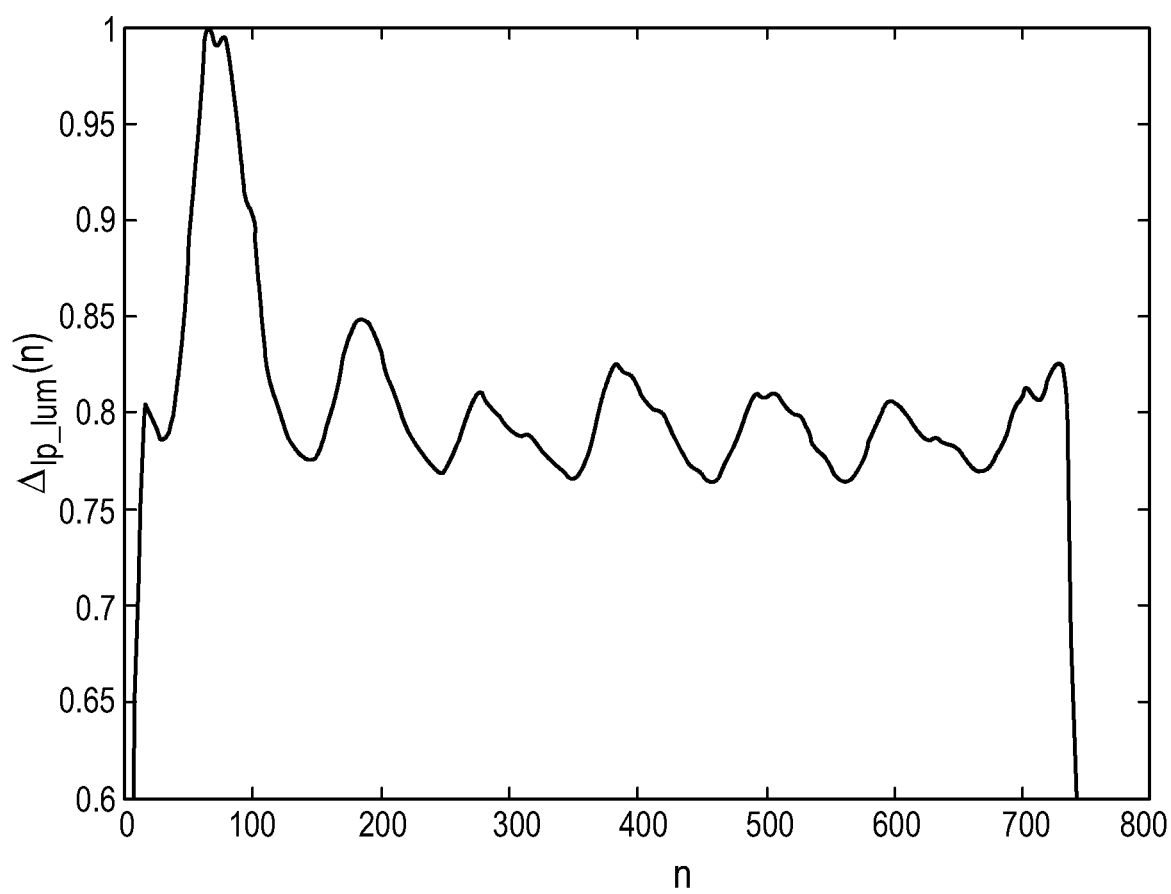
FIG. 6 shows schematically and exemplarily a strongly low-pass filtered respiratory motion signal.

The absolute frame difference $\Delta_{lp\_lum}(n)$, i.e. the respiratory motion signal, which has been convolved with the box or rectangle filter is schematically and exemplarily shown in FIG. 6 depending on the frame number n. This relatively strong low-pass filtering, in comparison to the slight low-pass filtering which led to the signal shown in FIG. 5, can also be performed by convolving the respiratory motion signal, i.e. the absolute frame difference, with another low-pass filter.

Figure 7:
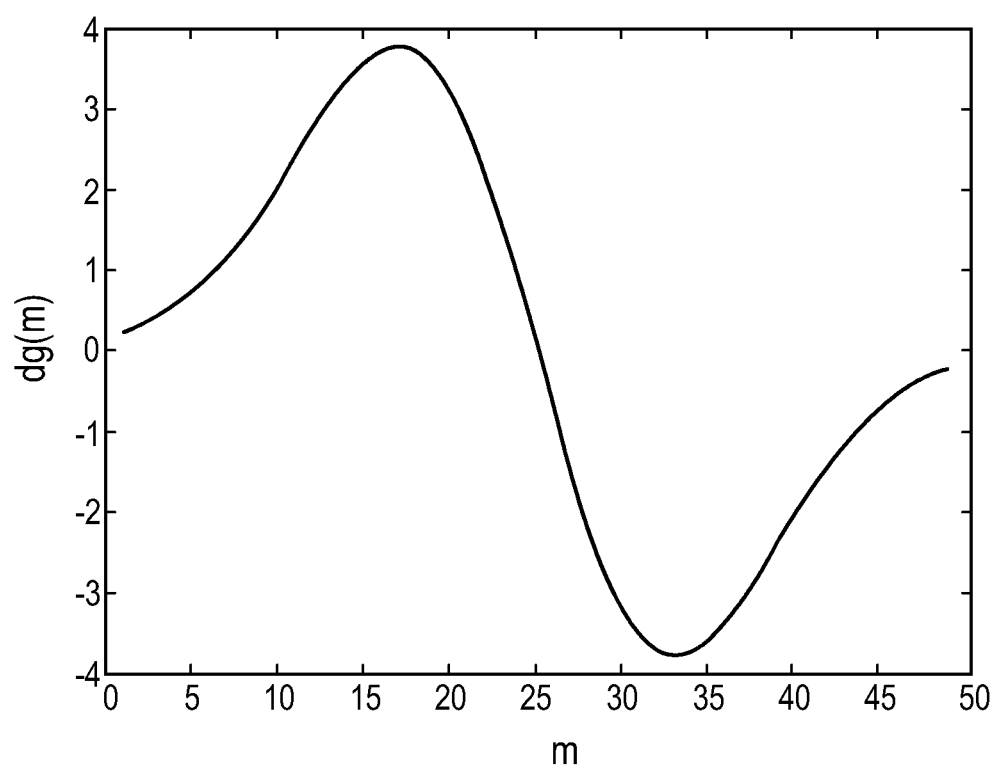
FIG. 7 shows schematically and exemplarily a first order Gaussian derivative.

In order to determine the local minima of the low-pass filtered respiratory motion signal shown in FIG. 6, the low-pass filtered respiratory motion signal can be convolved with the first order Gaussian derivative or similar filters and zero crossings of the resulting signal can be determined. A +/− zero crossing defines a local maximum and a −/+ zero crossing defines a low-frequent local minimum. The first order Gaussian derivative dg(m) is schematically and exemplarily shown in FIG. 7 and can be described by following equation:

$$dg(m) = \frac{-m}{\sqrt{2\pi\sigma^3}} e^{-\frac{m^2}{2\sigma^2}}, \tag{7}$$

wherein $$\sigma = 8, m = [-3\sigma, 3\sigma]. \tag{8}$$

The convolution of the low-pass filtered frame difference $\Delta_{lp\_lum}(n)$ with the first order Gaussian derivative can be described by following equation:

$$\Delta_{lp\_lum}(n) * dg(m) \tag{9}$$

The respiratory characteristics determination unit 9 is preferentially further adapted to determine the inhale/exhale transitions by determining the peaks of a valley-shaped streaming standard deviation close to the low-frequent maxima. As can be seen in FIG. 5, the inhale/exhale transitions are located in the closest neighborhood of the local maxima. Computing the streaming standard deviation signal will give a high response where the signal shows a higher frequency component. This is the case for the locations of the inhale/exhale transitions, but also for rapid inhale or exhale periods where, for example, a lot of air is inhaled/exhaled or air is inhaled/exhaled very fast. The respiratory characteristics determination unit 9 can therefore be adapted to calculate a streaming standard deviation of the respiratory motion signal and to weight the calculated streaming standard deviation before determining positions of peaks, wherein the weight for a calculated streaming standard deviation value is larger, if the corresponding respiratory motion signal value is located in a local minimum or valley of the respiratory motion signal, and wherein the weight for a calculated streaming standard deviation value is smaller, if the corresponding respiratory motion signal is not located in local minimum or valley of the respiratory motion signal. The larger weight is, for example, 1000 and the smaller weight is, for example, 1. For determining, whether a certain respiratory motion signal value is located in a local minimum or a valley of the respiratory motion signal, the respiratory characteristics determination unit 9 can be adapted to determine whether a) the sum of respiratory motion signal values in a first region close, in particular, around the certain respiratory motion signal value, is smaller than the sum of respiratory motion signal values in a second region being neighbored to the first region in a temporal backward direction and b) the sum of respiratory motion signal values in a third region close, in particular, around the certain respiratory motion signal value, is smaller than the sum of respiratory motion signal values in a fourth region being neighbored to the third region in a temporal forward direction. For example, if the certain respiratory motion signal value corresponds to the frame number n, the first region can be defined by the frame numbers n−1 and n, the second region can be defined by the frame numbers n−3 and n−2, the third region can be defined by the frame numbers n−1 and n, and the fourth region can be defined by the frame numbers n+3 and n+2. The first region and the third region can be the same.

Figure 8:
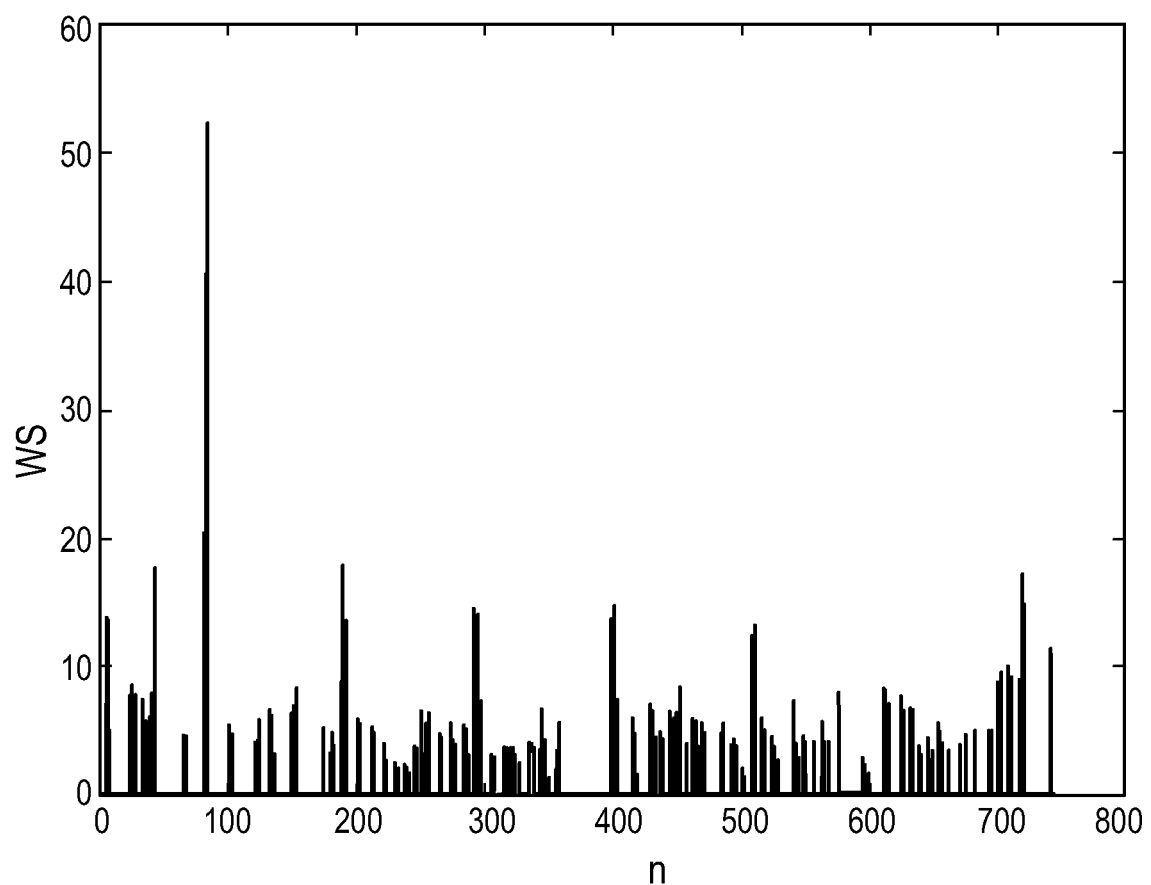
FIG. 8 shows schematically and exemplarily a valley-based weighted standard deviation.

FIG. 8 shows exemplarily a weighted streaming standard deviation WS depending on the frame number n.

The respiratory characteristics determination unit is preferentially adapted to determine local maxima of the weighted streaming standard deviation, to determine peak positions of peaks of the weighted streaming standard deviation having an amplitude larger than the predefined threshold, to determine for each local maximum of the local maxima a peak position among the determined peak positions, which is closest to the position of the respective local maximum, and to determine the inhale/exhale transitions from the determined peak positions. In particular, the inhale/exhale transitions are determined as the peaks in FIG. 8 which lie closest to the local maxima, wherein the local maxima are preferentially determined analogously to the local minima. The inhale/exhale transition points can be found by searching for the peaks in FIG. 8, which lie closest to the local maxima, because the inhale/exhale transitions points are located amid the local maxima.

Figure 9:
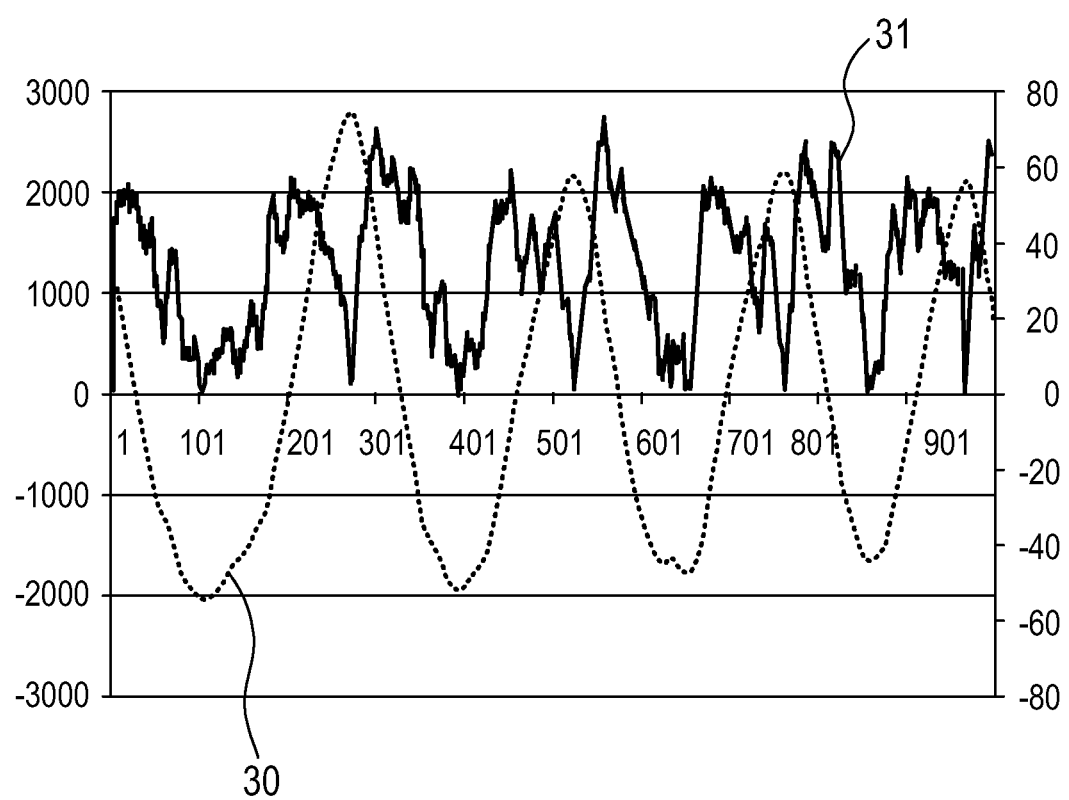
FIG. 9 shows schematically and exemplarily a chest expansion and an absolute temporal derivative of the chest expansion.

FIG. 9 shows schematically and exemplarily a chest expansion 30 as a function of time as measured, for example, during a magnetic resonance imaging scan with a pneumatic respiration belt in arbitrary units. Moreover, FIG. 9 shows the absolute temporal derivative 31 of the chest expansion 30 in arbitrary units. As can be seen in FIG. 9, the absolute temporal derivative 31 of the chest expansion 30 is correlated with the respiratory motion signal shown in FIG. 5. This shows that the temporal respiratory motion signal is virtually linearly proportional to the absolute value of the average velocity of the apparent motion of the illumination pattern.

Referring again to FIG. 1, the respiratory motion detection apparatus 1 further comprises an output unit 10 for outputting an output signal depending on the determined respiratory motion signal. In this embodiment, the output unit is adapted to output an output signal indirectly depending on the determined respiratory motion signal by outputting the output signal depending on the respiratory characteristic of the person 2 determined by the respiratory characteristics determination unit 9. However, in another embodiment the respiratory motion detection apparatus can also be adapted to allow the output unit to output an output signal directly depending on the determined respiratory motion signal. For example, the output unit can be adapted to influence the person's sleep/relaxation state by a change in sound, light, temperature and/or air composition provided by the output signal. Moreover, if the determined respiratory motion signal and/or the respiratory characteristic is indicative of irregularities in respiration, the person can be alerted by the output signal, and, for example, a doctor's visit can be suggested.

The illuminator 3 is preferentially located below the detector 4. For example, as schematically and exemplarily shown in FIG. 10, the illuminator and the detector can be integrated into a cylindrical arrangement 40. The cylindrical arrangement 40 comprises a lower part 43 and an upper part 44. In the lower part 43 an opening 45 is provided which allows infrared light 41 to leave the cylindrical arrangement 40 for illuminating the person with an infrared illumination pattern. The upper part 44 of the cylindrical arrangement 40 comprises an opening 46 for allowing light 42 reflected from the person to be reflected by a convex mirror 47 onto an infrared video camera for detecting the illumination pattern on the person. The convex mirror 47 is connected to the intermediate part of the cylindrical arrangement 40 via a holding element like a holding structure which is schematically indicated in FIG. 10 by the broken line 48.

Figure 10:
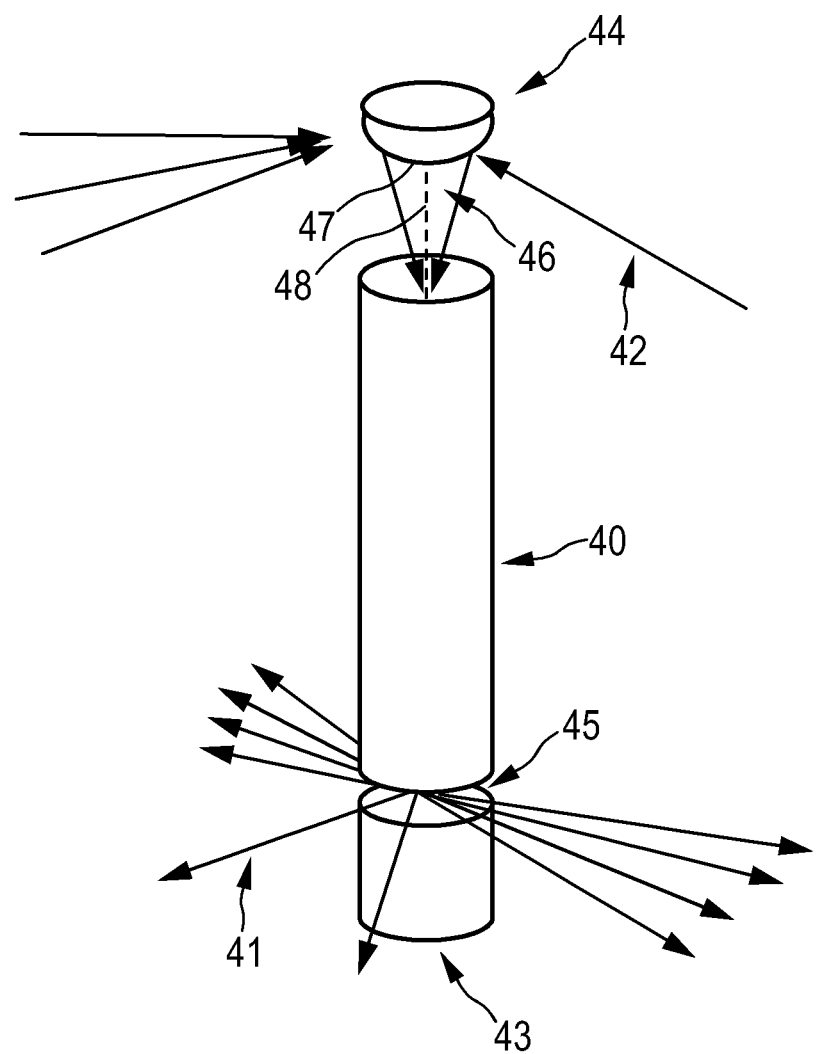
FIG. 10 shows schematically and exemplarily a cylindrical arrangement comprising an illuminator and a detector of a respiratory motion detection apparatus.

The cylindrical arrangement shown in FIG. 10 provides an omnidirectional detection of breathing motion of a sleeping person lying on a bed under a blanket. As such, an ease of installation and robustness against the positioning with respect to the sleeping subject is provided. A video camera within the cylindrical arrangement observes the convex mirror 47 for capturing an omnidirectional video image of the scene with the projected illumination pattern. The cylindrical structure can be modified such that several illumination patterns of infrared light are allowed to escape through openings at various elevations, wherein at each elevation a circular symmetric light cone is emitted, which is aiming slightly downward. Each circular symmetric light cone can be adapted to project a circular symmetric repetitive pattern of lines being an illumination pattern. The video camera is then preferentially adapted to capture an omnidirectional image of the scene with the projected illumination patterns.

Figure 11:
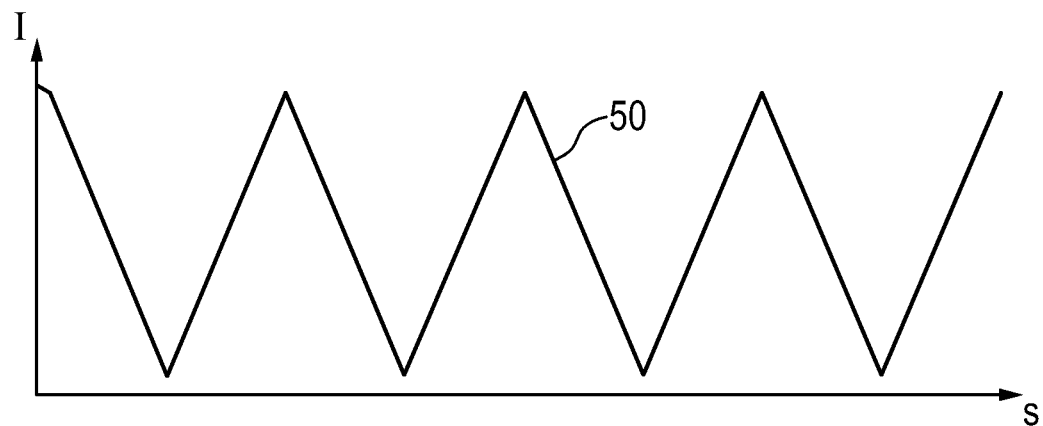
FIG. 11 shows exemplarily and schematically a saw-tooth illumination pattern.

As already mentioned above, the illumination pattern can be a saw-tooth pattern. Such a saw-tooth pattern 50 is schematically and exemplarily shown in FIG. 11. In FIG. 11 the vertical dimension is the light intensity I and the horizontal dimension is a spatial dimension.

The respiratory motion detection apparatus can comprise a respiratory motion filtering unit for filtering the temporal respiratory motion signal such that influences on the temporal respiratory motion signal due to other motions of the person are reduced, in particular, eliminated.

Figure 12:
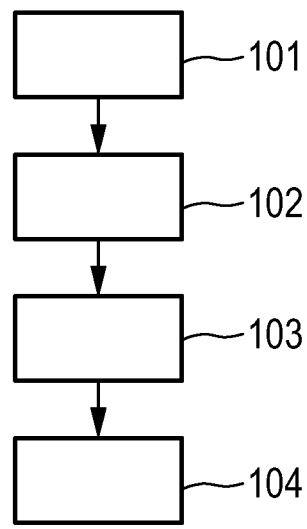
FIG. 12 shows a flowchart exemplarily illustrating an embodiment of a respiratory motion detection method for detecting respiratory motion of a person.

In the following an embodiment of a respiratory motion detection method for detecting respiratory motion of a person will be described with reference to a flowchart shown in FIG. 12.

In step 101, the person 2 is illuminated with an illumination pattern 11 by the illuminator 3, and in step 102 the illumination pattern 11 on the person 2 is detected over time. Preferentially, the person 2, in particular, a blanket 6 covering the person 2, is illuminated by an infrared illumination pattern and a video of this infrared illumination pattern on the person is captured. In step 103, a respiratory motion signal being indicative of the respiratory motion of the person is determined from the detected illumination pattern. In particular, the absolute frame difference is determined in accordance with equation (5) as the respiratory motion signal. In step 104, a respiratory characteristic of the person like the inhale/exhale transitions or the exhale/inhale transitions of the person are determined from the determined temporal respiratory motion signal. Step 104 can be omitted and the respiratory motion signal determined in step 103 can be used for other purposes, in particular, can just be shown on a display.

Although in the above described embodiments, the respiratory motion detection apparatus is adapted to detect the respiratory motion of a single person, the respiratory motion detection apparatus can also be adapted to detect the respiratory motion of several persons. In this case, the illuminator is preferentially adapted to illuminate the several persons by the illumination pattern and the respiratory motion signal determination unit is preferentially adapted to assign different regions of the detected illumination pattern to the several persons and to determine a respiratory motion signal of a person of the several persons from the region of the detected illumination pattern assigned to the respective person. Thus, different spatial regions of the detected illumination pattern, i.e. of a video showing the deformations of the illumination pattern, are identified and assigned to the several persons, and the respiratory motion signals of the persons are determined based on the deformations of the illumination pattern in the different spatial regions of the detected illumination pattern. This allows the respiratory motion detection apparatus to determine the respiratory motions of the different person in a room, in particular, lying in one or multiple beds. The separation of the different respiratory motion signals is therefore preferentially based on a segmentation of a video frame in separate spatial regions, wherein the easiest implementation of such an image segmentation is a manual annotation by drawing the contours of the separate regions of interest. However, also automatic segmentation algorithms can be used for automatically segmenting the video frames in different regions associated with different persons. For example, based on the occurrence of estimated motion vectors, which can be estimated from images of the illumination pattern as, for example, described in the article "True-motion estimation with 3-D recursive search block matching", G. de Haan, P.W.A.C. Biezen, H. Huijgen, O. A. Ojo, IEEE Transactions on Circuits and Systems for Video Technology, pages. 368-379, October. 1993, persons present in the images can be segmented and their breathing motion can be analyzed separately. The analysis for determining separate respiratory motion signals for different persons can also be performed by blind-source separation using multiple projectors, for example, multiple illuminators.

In a further embodiment of the respiratory motion detection apparatus, which also provides the possibility to follow the respiratory motion of multiple persons, the respiratory motion signal determination unit is adapted to determine firstly a temporal respiratory motion signal, which is preferentially the absolute frame difference, for all persons and to separate the firstly determined respiratory motion signal in several respiratory motion subsignals, which can be assigned to the different persons, based on an analysis of the firstly determined overall temporal respiratory motion signal. In case the captured projected illumination pattern covers multiple breathing subjects, i.e. multiple persons, the firstly determined temporal respiratory motion signal essentially contains the sum of the individual respiratory motion subsignals. As each individual respiratory motion subsignal tends to be different, but characteristic to the individual person, the firstly determined temporal respiratory motion can be separated into its individual components, i.e. its individual respiratory motion subsignals. Various methods are available for such signal decomposition such as the principal component analysis.

The respiratory motion signal, which is preferentially a data stream, can be used to interact with the person or with an external device. Moreover, the respiratory motion signal can be combined with data streams of other sensory devices.

The illuminator of the respiratory motion determination apparatus is preferentially and infrared light source, in particular, a near infrared light source. Correspondingly, the detector can be a consumer camera or a webcam, which use a daylight cut filter, in order to detect the near infrared range of the spectrum.

In the healthcare domain the diagnosis of sleep/respiratory disorders and cardiac diseases can be assisted and brought closer to the patient due to the system's ease of use and unobtrusiveness while still letting him enjoy his natural sleeping environment since no on-body sensors are needed.

The respiratory motion detection apparatus and method can be used for sensing sleep in the healthcare domain and in the diagnosis of sleep disorders. However, the respiratory motion detection apparatus and method can also be used in the consumer lifestyle areas as opportunity areas for sleep enhancement products. By analyzing the respiration of a sleeping person lighter sleep phases and REM sleep can be identified as described in, for example, the article "Control of breathing in health and disease", Murray D. Altose, Yoshikazu Kawakami, Vol. 135, ISBN: 0-8247-9854-6, 1999.

The right wake-up moment of the body can thus be determined and let the user start his day with a boost of energy and a good mood. Another application would be to find the right moment to deepen one's sleep throughout the night. When a person is entering a lighter sleep phase, external stimuli such as temperature increase/decrease in the bed could be applied to deepen one's sleep. Furthermore, unobtrusive respiration analysis can assist in the area of Relaxation for Sleep where unobtrusive sensors are desired since a person can perform the relaxation exercises while lying in bed and can fall asleep smoothly without having to unhook on-body sensors or turn off the system.

The respiratory motion detection apparatus and method preferentially allow measuring the subtle respiratory motion automatically. They are preferentially based on video and use an infrared light pattern that is invisible to the human eye. The respiratory motion detection apparatus and method are preferentially capable of detecting every respiration cycle, the period of inhaling, the period of exhaling and both the inhale/exhale and exhale/inhale transitions. A remote analysis of the respiratory functions is valuable both in the medical field and in consumer lifestyle. The symptoms of a large number of diseases like respiratory diseases and cardiac diseases can be observed in the subject's breathing pattern. In the lifestyle area, the proposed system can be employed as an improved relaxation solution or a sleep improvement control tool.

In Healthcare, a large number of diseases (e.g. heart failure, respiratory or lung diseases, kidney failure) can be recognized by analyzing the respiratory pattern. For example, when heart failure is advanced, Cheyne-Stokes respiration (periodic breathing) may develop. Symptoms of heart failure may begin suddenly, especially if the cause is a heart attack. However, most people have no symptoms when the heart first begins to develop problems. Symptoms then develop gradually over days to months or years. The most common symptoms are shortness of breath and fatigue. Heart failure may stabilize for periods of time but often progresses slowly and insidiously.

Right-sided heart failure and left-sided heart failure produce different symptoms. Although both types of heart failure may be present, the symptoms of failure of one side often predominate. Eventually, left-sided heart failure causes right-sided failure. Left-sided heart failure leads to fluid accumulation in the lungs, which causes shortness of breath. At first, shortness of breath occurs only during exertion, but as heart failure progresses, it occurs with less and less exertion and eventually occurs even at rest. People with severe left-sided heart failure may be short of breath when lying down (a condition called orthopnea), because gravity causes more fluid to move into the lungs. Sitting up causes some of the fluid to drain to the bottom of the lungs and makes breathing easier.

When heart failure is advanced, Cheyne-Stokes respiration (periodic breathing) may develop. In this unusual pattern of breathing, a person breathes rapidly and deeply, then more slowly, then not at all for several seconds. Cheyne-Stokes respiration develops because blood flow to the brain is reduced and the areas of the brain that control breathing therefore do not receive enough oxygen.

Some people with heart failure experience orthopnea, paroxysmal nocturnal dyspnea, or both. Orthopnea is shortness of breath when a person lies down that is relieved by sitting up. Paroxysmal nocturnal dyspnea is a sudden, often terrifying, attack of shortness of breath during sleep. This condition is an extreme form of orthopnea and a sign of severe heart failure.

Dyspnea can also occur in people who have anemia or blood loss because of a decreased number of red blood cells, which carry oxygen to the tissues. The person breathes rapidly and deeply, in a reflex effort to try to increase the amount of oxygen in the blood.

Someone with severe kidney failure or sudden worsening of diabetes mellitus or someone who has taken certain drugs or poisons feels out of breath and may begin to pant quickly because of an accumulation of a large amount of acids in the blood (a condition called metabolic acidosis). Anemia and heart failure may also contribute to dyspnea in people with kidney failure.

Besides cardiac diseases, which can be observed in the respiratory pattern, respiratory diseases are wide spread, where an early intervention or more straightforward diagnosis would be beneficial for both a person's health and the healthcare cost. The British Lung Foundation reveals that there are more than 40 conditions which affect the lungs and/or airways and impact on a person's ability to breathe. They include lung cancer, tuberculosis, asthma, COPD (chronic obstructive pulmonary disease), cystic fibrosis, sleep apnoea, avian flu, bronchiolitis and many others.

Respiration control is valuable in the field of Consumer Lifestyle, particularly for relaxation. Nowadays, it is more difficult to fall asleep in a relaxed manner due to irregular sleep, shift duty, performance pressure and stress. Solutions around relaxation become more and more important. A person's state of relaxation is closely linked to his/her breathing characteristics. Since the breathing pattern changes throughout the process of falling asleep, respiration analysis can provide control parameters for sleep enhancement interventions, such as paced breathing for relaxation.

A third area of interest for the proposed system is to use the breathing analysis to improve a person's sleep quality. We spend almost a third of our life sleeping. Good quality sleep is essential for good health and well-being. However, lifestyle and environmental factors are increasingly causing difficulties in sleeping. Nowadays, there is an increased deterioration of sleep quality due to diseases, irregular sleep, shift duty, performance pressure, and stress. Bad sleep has negative effects on our behaviour, mood, performance, safety (prone to accidents), mental and physical health.

Sleep stages or wake/sleep states and breathing characteristics are linked. This information can be used to influence a person's sleep and improve herewith his/her sleep quality. The proposed remote sensing technique can thus not only be used for diagnosis of diseases but also as an improved relaxation solution or a sleep improvement control tool.

In the prior art, typically, the respiration is monitored and measured with a respiratory inductance plethymography belt, which is worn around the chest.

In order to let a person enjoy his/her natural sleeping environment, the respiratory motion detection apparatus and method can be adapted to provide a remote technology which can provide the breathing rate, both the inhale-exhale and exhale-inhale transition times, the period of exhaling, and the period of inhaling.

The proposed device can be setup by a layman in a straightforward manner which makes a wide spread and use of respiration monitoring devices possible. The recorded data can be sent to a specialist who can intervene at an early stage of e.g. heart failure in order to prevent further worsening of the disease.

In the field of Consumer Lifestyle, breathing can be used as a relaxation tool in order to reduce stress, eliminate tension throughout the body and achieve a calm and peaceful state of mind. Various products on the market offer touch sensors with which biofeedback (of e.g. the respiratory characteristics) is given to the consumer. However, on-body sensors for respiration analysis are not preferred by the consumer since they are uncomfortable and inconvenient. In contrast, the respiratory motion detection apparatus and method allow to determine the respiratory motion in a contact-less way.

The respiratory motion detection method is preferentially invariant to the location of the detector as long as the person, in particular, the chest area is visible (above or under blanket) in the image and preferentially does not require any training and data sets before-hand. Hidden body parts (by e.g. blanket or other body parts) do not pose critical limitations to the performance of the suggested method. Experiments have shown that the pattern deformation is visible with thin and thick blankets, and different positions of the lying person (on the back, on the side, on the belly).

The respiratory motion detection apparatus and method can be adapted such that respiratory characteristics can be determined, which are indetectable by known methods due to the sub-pixel motion amplitude.

The quantification of the apparent motion by the configuration described above with reference to FIG. 4 is comparable to phase-shifting interferometry which is typically used for quantification of depth and disclosed in, for example, the article of "Phase-Shifting Interferometry", J. C. Wyant, University of Arizona, Course material, 1998. The high-motion detection is preferentially achieved by creating a distance, a "baseline", between the illuminator and the detector.

Although in an above described embodiment inhale/exhale transitions have been determined by using a streaming standard deviation, in other embodiments respiratory characteristics, in particular, inhale/exhale transitions, can be determined without using a streaming standard deviation. For example, the SAD can directly be used for determining respiratory characteristics, without performing the streaming standard deviation.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The determinations like the determination of the respiratory motion signal and the determination of respiratory characteristics performed by one or several units or devices can be performed by any other number of units or devices. For example, steps 103 and 104 can be performed by a single unit or by any other number of different units. The determinations, in particular, the calculations, and/or the control of the respiratory motion detection apparatus in accordance with the respiratory motion detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a respiratory motion detection apparatus for detecting respiratory motion of a person. An illuminator illuminates the person with an illumination pattern, and a detector detects the illumination pattern on the person over time. A temporal respiratory motion signal being indicative of the respiratory motion of the person is determined from the detected illumination pattern by a respiratory motion signal determination unit. The illumination pattern deforms significantly with slight movements of the person. Thus, since the respiratory motion signal determination unit is adapted to determine the temporal respiratory motion signal from the detected illumination pattern, even slight respiratory movements of the person can be determined. The sensitivity of detecting respiratory movements of a person can therefore be improved.

The invention claimed is:

1. A respiratory motion detection apparatus for detecting respiratory motion of at least one person, the respiratory motion detection apparatus comprising:
   an illuminator,
      wherein the illuminator is arranged to illuminate the at least one person with an illumination pattern,
      wherein the illumination pattern has an intensity,
      wherein the intensity varies along a spatial axis;
   a detector, wherein the detector is arranged to detect the illumination pattern on the at least one person over time;
   a respiratory motion signal determination circuit,
      wherein the respiratory motion signal determination circuit is arranged to determine a temporal respiratory motion signal,
      wherein the temporal respiratory motion signal is indicative of the respiratory motion of the at least one person from the detected illumination pattern; and
   a respiratory characteristics determination circuit,
      wherein the respiratory characteristics determination circuit is configured to calculate a standard deviation signal of the temporal respiratory motion signal,
      wherein the respiratory characteristics determination circuit is arranged to determine inhale/exhale transitions and exhale/inhale transitions from at least the standard deviation signal,
   wherein the respiratory characteristics determination circuit is further configured to determine a local maxima of the calculated standard deviation signal,
   wherein the respiratory characteristics determination circuit is further configured
   to determine peak positions of peaks of the calculated standard deviation signal having an amplitude larger than a predefined threshold,
   wherein the respiratory characteristics determination circuit is further configured
   to determine the inhale/exhale transitions from the determined peak positions.

2. The respiratory motion detection apparatus as defined in claim 1,
   wherein the illuminator is arranged to illuminate the at least one person in an illumination direction,
   wherein the detector is arranged to detect the illumination pattern on the at least one person in a detection direction,
   wherein the illumination direction and the detection direction are different.

3. The respiratory motion detection apparatus as defined in claim 2,
   wherein the illuminator is arranged to illuminate a surface of the at least one person with the illumination pattern under an illumination angle,
   wherein the illumination angle is defined as the angle between the illumination direction and a perpendicular axis,
   wherein the perpendicular axis is perpendicular to the illuminated surface,
   wherein the detector is arranged to detect the illumination pattern on the surface under a detection angle,
   wherein the detection angle is defined as the angle between the detection direction and the perpendicular axis,
   wherein the illumination angle is larger than the detection angle.

4. The respiratory motion detection apparatus as defined in claim 1,
   wherein the detector is arranged to detect a plurality of temporally consecutive images of the illumination pattern,
   wherein the respiratory motion signal determination circuit is arranged to determine the temporal respiratory motion signal depending on a sum of absolute differences of image values,
   wherein the absolute difference of image values are of corresponding spatial positions in the plurality of temporally consecutive images.

5. The respiratory motion detection apparatus as defined in claim 1, wherein the respiratory characteristics determination circuit is further configured to determine the inhale/exhale transitions and exhale/inhale transitions depending on times at which the temporal respiratory motion signal shows a local minimum.

6. The respiratory motion detection apparatus as defined in claim 1, wherein the respiratory characteristics determination circuit is further configured to determine the inhale/exhale transitions by converting the temporal respiratory motion signal in a frequency domain and identifying local minima in the filtered respiratory motion signal.

7. The respiratory motion detection apparatus as defined in claim 6,
   wherein the respiratory characteristics determination circuit is further configured to low-pass filter the temporal respiratory motion signal,
   wherein the respiratory characteristics determination circuit is further configured to determine the local minima of the low-pass filtered temporal respiratory motion signal,
   wherein the respiratory characteristics determination circuit is further configured to determine exhale/inhale transitions from the determined local minima.

8. A respiratory motion detection apparatus for detecting respiratory motion of a person, the respiratory motion detection apparatus comprising:
   an illuminator,
      wherein the illuminator is arranged to illuminate the person with an illumination pattern,
      wherein the illumination pattern has an intensity that varies along a spatial axis in a manner of at least one of a sinusoid and a saw-tooth;
   a detector, wherein the detector is arranged to detect the illumination pattern on the person over time;
   a respiratory motion signal determination circuit,
      wherein the respiratory motion signal determination circuit is arranged to determine a temporal respiratory motion signal,
      wherein the temporal respiratory motion signal is indicative of the respiratory motion of the person from the detected illumination pattern; and
   a respiratory characteristics determination circuit,
      wherein the respiratory characteristics determination circuit is arranged to determine a respiratory characteristic of the person from the determined temporal respiratory motion signal,
      wherein the respiratory characteristics determination circuit is arranged to calculate a standard deviation signal of the temporal respiratory motion signal,
      wherein the respiratory characteristics determination circuit is arranged to determine a local maxima of the standard deviation signal, wherein the respiratory characteristics determination circuit is arranged to determine peak positions of peaks of the standard deviation signal, wherein the a portion of the determined peak positions have an amplitude larger than a predefined threshold, wherein the respiratory characteristics determination circuit is arranged to determine a first peak position from the portion of the determined peak positions, wherein the first peak position is closest to the position of the local maxima, wherein the respiratory characteristics determination circuit is arranged to determine inhale/exhale transitions from the portion of the determined peak positions.

9. The respiratory motion detection apparatus as defined in claim 8, wherein the respiratory characteristics determination circuit is further configured to weight the standard deviation signal before determining the peak positions of peaks, wherein the weight for the standard deviation signal is larger, if a corresponding temporal respiratory motion signal value is located in a local minimum of the temporal respiratory motion signal, wherein the weight for the standard deviation signal value is smaller, if the corresponding temporal respiratory motion signal value is not located in a local minimum of the temporal respiratory motion signal.

10. The respiratory motion detection apparatus as defined in claim 1, wherein the respiratory motion detection apparatus is further configured to detect the respiratory motion of several persons, wherein the illuminator is arranged to illuminate the several persons with the illumination pattern, wherein the respiratory motion signal determination circuit is arranged to assign different regions of the detected illumination pattern to the several persons, wherein respiratory motion signal determination circuit is arranged to determine the respiratory motion of a person of the several persons from the region of the detected illumination pattern assigned to the respective person.

11. A method for detecting respiratory motion of a person and altering an environmental factor, the method comprising:

illuminating, using an illuminator controlled by a processor circuit, the person with an illumination pattern that varies along a spatial axis, detecting, using a detector providing data to the processor circuit, the illumination pattern on the person over time, determining, a respiratory motion signal, wherein the respiratory motion signal is indicative of the respiratory motion of the person from the detected illumination pattern;

calculating a standard deviation signal of the respiratory motion signal;

determining inhale/exhale transitions and exhale/inhale transitions from the standard deviation signal; and altering, autonomously, using the processor circuit, the environmental factor in response to the determined respiratory motion signal, wherein the environmental factor is selected from the group consisting of sound, light, temperature and air composition wherein the standard deviation signal comprises a local maxima of the standard deviation signal, wherein at least one peak position of peaks of the standard deviation signal have an amplitude larger than a predefined threshold, wherein the determining inhale/exhale transitions is configured to determine the inhale/exhale transitions from the at least one peak position.

12. The respiratory motion detection apparatus as defined in claim 1, further comprising a processor circuit, wherein the processor circuit is configured to control the illuminator, the detector, and the respiratory motion signal determination circuit.

13. A non-transitory computer-readable storage-medium comprising instructions that when executed by a processor circuit perform a method for altering an environmental factor in response to detecting respiratory motion of a person, the method comprising:

illuminating, the person with an illumination pattern that varies along a spatial axis, detecting, the illumination pattern on the person over time, determining a respiratory motion signal, wherein the respiratory motion signal is indicative of the respiratory motion of the person from the detected illumination pattern;

calculating a standard deviation signal of the respiratory motion signal;

determining inhale/exhale transitions and exhale/inhale transitions from the standard deviation signal; and altering, autonomously, the environmental factor in response to the determined respiratory motion signal, wherein the environmental factor is selected from the group consisting of sound, light, temperature and air composition.

14. The respiratory motion detection apparatus of claim 1, wherein the illuminator comprises a light source, wherein the light source is configured to generate ultraviolet light, wherein the ultraviolet light is arranged to illuminate the person.

15. The respiratory motion detection apparatus of claim 14, wherein the illuminator comprises a spatial modulator, wherein the spatial modulator comprises an attenuation mask.

16. The method of claim 11, wherein the illuminator comprises a light source configured to generate ultraviolet light, wherein ultraviolet light is arranged to illuminate the person.

17. The method of claim 16, wherein the illuminator comprises a spatial modulator, wherein the spatial modulator comprises an attenuation mask.

* * * * *